United States Patent [19]

Benko et al.

[11] 4,404,204

[45] Sep. 13, 1983

[54] PYRIDAZINO[4,5-B]QUINOXALINE-5,10-DIOXIDE DERIVATIVES, A PROCESS FOR PREPARING SAME AND ANTI-MICROBIAL COMPOSITIONS CONTAINING SAME

[75] Inventors: Pal Benko; Daniel Bozsing; Janos Gundel; Karoly Magyar, all of Budapest, Hungary

[73] Assignee: Patentbureau DANUBIA, Hungary

[21] Appl. No.: 275,393

[22] Filed: Jun. 19, 1981

[30] Foreign Application Priority Data

Jul. 25, 1980 [HU] Hungary .............................. 1862/80

[51] Int. Cl.³ .................. C07D 487/04; C07D 241/52; C07D 401/12; A61K 31/495
[52] U.S. Cl. .................................... 424/250; 544/234; 544/355; 426/532
[58] Field of Search ........................ 544/234; 426/532; 424/250

[56] References Cited

U.S. PATENT DOCUMENTS 4,303,657 12/1981 Young .................................. 544/353

OTHER PUBLICATIONS

Monge et al., Chem. Abs. 86, 12/290d (1976).

Primary Examiner—Mark L. Berch
Attorney, Agent, or Firm—Keil & Witherspoon

[57] ABSTRACT

The invention relates to fodder concentrates, fodder additives and fodders having antimicrobial and/or weight-gain increasing effects which comprise as active ingredient a new compound of the general formula (I)

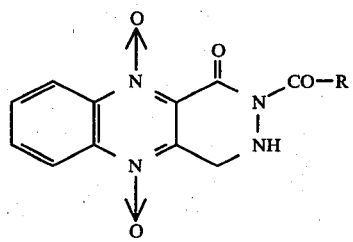

/I/ wherein
R represents a $C_{1-20}$ alkyl, a $C_{1-6}$ alkoxy group, an optionally substituted $C_{6-10}$ aryl group, a phenyl-($C_{1-3}$ alkyl), a $C_{3-7}$ cycloalkyl or a 5 or 6 membered heterocyclic group containing one or two nitrogen and/or oxygen and/or sulfur atom(s),
or a biologically acceptable acid addition salt of a basic compound of the general formula (I) together with a suitable inert, solid or liquid carrier or diluent.

The invention relates also to the preparation of the new compounds of the general formula (I).

6 Claims, No Drawings

PYRIDAZINO[4,5-B]QUINOXALINE-5,10-DIOXIDE DERIVATIVES, A PROCESS FOR PREPARING SAME AND ANTI-MICROBIAL COMPOSITIONS CONTAINING SAME

The invention relates to new pyridazino [4,5-b]-quinoxaline-5,10-dioxide derivatives, a process for the preparation thereof and compositions-particularly feed additives, fodder concentrates and animal feeds-containing the same.

It is known that certain quinoxaline-1,4-dioxide derivatives possess antimicrobial and weight-gain increasing properties. Such compounds are described in U.S. Pat. No. 3,371,090, Belgian patent No. 764,088 and GFR Pat. No. 1,670,930. Condensed quinoxaline-1,4-dioxide derivatives are disclosed in British Pat. No. 1,303,372.

According to the present invention there are provided new pyridazino [4,5-b] quinoxaline-5,10-dioxide derivatives of the general formula (I)

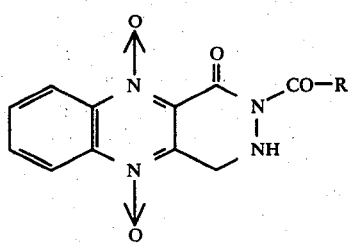

/I/ wherein

R represents a $C_{1-20}$ alkyl, a $C_{1-6}$ alkoxy group, an optionally substituted $C_{6-10}$ aryl group, a phenyl-($C_{1-3}$ alkyl), a $C_{3-7}$ cycloalkyl or a 5 or 6 membered heterocyclic group containing one or two nitrogen and/or oxygen and/or sulfur atom(s), and biologically acceptable acid addition salts of the basic compounds of the general formula (I).

The term "$C_{1-20}$ alkyl" refers to straight-chained or branched saturated aliphatic hydrocarbons containing 1–20 carbon atoms (e.g. methyl, ethyl, n-propyl, isopropyl, n-butyl, isobutyl, n-pentyl, n-decyl, n-dodecyl, stearyl, etc.). The "$C_{1-6}$ alkoxy groups" can be straight-chained or branched (e.g. methoxy, ethoxy, n-propoxy, isopropoxy, etc.). The "$C_{6-10}$ aryl group" can be phenyl or naphtyl and optionally contains one or more identical or different substituent(s) (e.g. $C_{1-6}$ alkoxy, $C_{1-6}$ alkyl group(s), nitro, amino and/or hydroxy group(s) and/or halogen atom(s). The "phenyl-($C_{1-3}$ alkyl) group" may represent e.g. benzyl, α-phenyl-ethyl, β-phenyl-ethyl, β,β-diphenyl-ethyl. The "5 or 6 membered heterocyclic group containing one or two nitrogen and/or oxygen and/or sulfur atom(s)" can be e.g. 2-, 3- or 4-pyridyl, pyrimidinyl, pyrazinyl, pyridazinyl, furyl, thienyl, thiazolyl, imidazolyl, etc. The "$C_{3-7}$ cycloalkyl group" may represent e.g. cyclopentyl or cyclohexyl. The term "halogen atom" encompasses all the four halogen atoms, i.e. fluorine, chlorine, bromine or iodine.

The compounds of the general formula (I) of basic character can form acid addition salts. Biologically acceptable inorganic acids (e.g. hydrochloric, hydrobromic, sulfuric acid, etc.) or organic acids (e.g. malic, maleinic, fumaric, tartaric, lactic, succinic acid, etc.) are suitable for salt formation.

Preferred representatives of the compounds of the general formula (I) are the compounds described in the Examples. Particularly preferred representatives are the following compounds:

2-methoxycarbonyl-1,2,3,4-tetrahydro-1-oxo-1H-pyridazino[4,5-b]-quinoxaline-5,10-dioxide, 2-isonicotinoyl-1,2,3,4-tetrahydro-1-oxo-1H-pyridazino[4,5-b]quinoxaline-5,10-dioxide, and biologically acceptable acid addition salts of the latter compound.

According to a further feature of the invention there is provided a process for the preparation of compounds of the general formula (I) and biologically acceptable acid addition salts thereof, characterized by a. reacting a compound of the general formula (II)

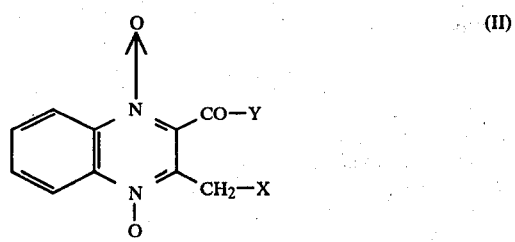

wherein

Y is a leaving group and X stands for halogen, with a compound of the general formula (III)

NH$_2$—NH—CO—R (III)

wherein R has the same meanings as above, or b. reacting the compound of the formula (IV)

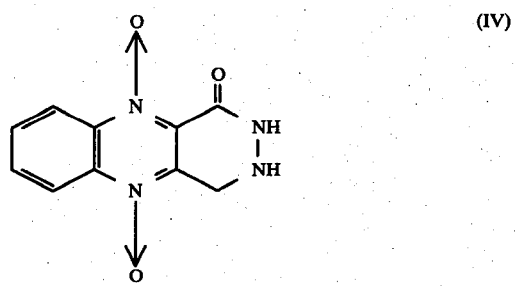

with an acylating agent of the general formula (V)

R—CO—Y' (V)

wherein Y' is a leaving group and R has the above defined meanings, or c. cyclizating a compound of the general formula (VI)

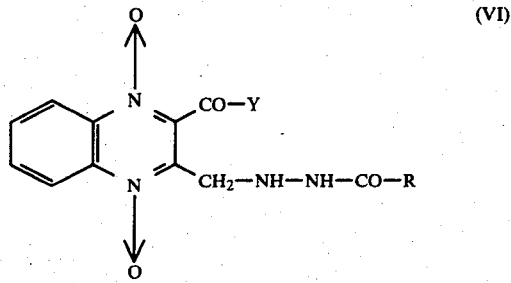

wherein

Y is a leaving group and R has the above defined meanings, or d. halogenating a compound of the general formula (VII)

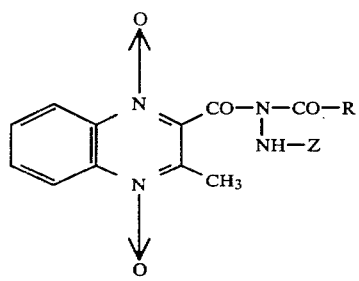

wherein
Z is a leaving group and R has the same meanings as above,
on the methyl group and subjecting the halomethyl derivative thus-obtained, after or without isolation, to cyclization, or e. oxidizing a compound of the general formula (VIII)

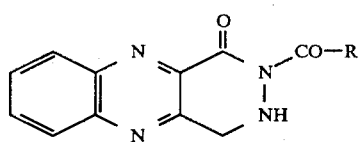

wherein R has the same meanings as above, and, if desired, converting the basic compound of the general formula (I) thus-obtained into a biologically acceptable acid addition salt.

According to variant a. of the process according to the invention a compound of the general formula (II) is reacted with a compound of the general formula (III). The halogen atom represented by the symbol X in the general formula (II) is preferably chlorine or bromine, and Y is any usual leaving group, e.g. $C_{1-6}$ alkoxy (such as methoxy, ethoxy), a halogen atom (such as chlorine or bromine), a sulfonyl group (e.g. $C_{1-6}$ alkylsulfonyloxy such as methanesulfonyloxy, or a preferably substituted arylsulfonyloxy group such as p-methyl-phenylsulfonyloxy or p-bromophenylsulfonyloxy), amino or substituted amino (e.g. mono- or di-($C_{1-6}$ alkyl)-amino such as methylamino, ethylamino, dimethylamino, etc.). The reaction is preferably performed in the presence of an acid binding agent. For this purpose inorganic or organic bases are suitable, such as alkali carbonates, alkali hydroxides, alkali bicarbonates, triethylamine, dimethylaniline, etc. The reaction is carried out at a temperature between 0° C. and the boiling point of the reaction mixture, preferably at about 20° C.–70° C.

One proceeds preferably in an inert organic solvent. As reaction medium preferably ethers (e.g. diethylether, dioxane, tetrahydrofurane, etc.), lower dialkylformamides (e.g. dimethylformamide), aliphatic or aromatic hydrocarbons (e.g. hexane, heptane, benzene, toluene or xylene, etc.), halogenated aliphatic or aromatic hydrocarbons (e.g. chloroform, methylene chloride, hydrocarbon tetrachloride, chlorobenzene, etc.), nitrated hydrocarbons (e.g. nitromethane, nitrobenzene, etc.), lower alkylnitriles (e.g. acetonitrile), heteroaromatic compounds (such as pyridine, chinoline, etc.), aliphatic alkanols (e.g. isopropanol, etc.) or the mixtures thereof can be used.

According to variant b. of the process according to the invention a compound of the general formula (IV) is acylated with an acylating agent of the general formula (V). As acylating agent the carboxylic acids of the general formula (V), the corresponding acid halides (Y' represents halogen, preferably chlorine or bromine), esters (Y' is lower alkoxy, preferably methoxy or ethoxy), anhydrides (Y' stands for lower alkanoyloxy), mixed anhydrides or amides (Y' is amino, mono- or di-($C_{1-6}$ alkyl)-amino, etc.) or other suitable reactive acid derivatives are suitable. The reaction is generally carried out in the presence of an acid binding agent. For this purpose the bases listed at variant a., particularly triethylamine can be used. When using a free carboxylic acid of the general formula (V), wherein Y' is hydroxy as acylating agent, the reaction is performed in the presence of a dehydrating agent (e.g. dicyclohexylcarbodiimide).

When using an acylating agent of the general formula (V), wherein R is a basic group, the presence of an acid binding agent is not necessary. The acylation is preferably carried out under heating. As reaction medium, the inert solvents listed at variant a. are suitable.

According to variant c. of the process according to the invention a compound of the general formula (VI) is cyclizated. In this formula Y represents groups defined at variant a., preferably $C_{1-6}$ alkoxy, particularly methoxy or ethoxy. The cyclization is carried out under circumstances generally applied at intramolecular cyclizations. When using a starting substance of the general formula (VI), wherein Y is a leaving group of acidic character (e.g. halogen atom), one proceeds preferably in the presence of an acid binding agent. When using a starting substance of the general formula (VI), wherein Y is a leaving group of neutral character (e.g. sulfonyloxy group such as p-toluenesulfonyloxy), one proceeds preferably in basic medium. When using a starting substance of the general formula (VI), wherein Y is a leaving group of basic character (e.g. amino), the presence of an acid binding agent is not necessary.

The ring closure is carried out under heating, preferably between 60° C. and the boiling point of the reaction mixture. As reaction medium, any solvent mentioned at variant a. is suitable. Any solvent inert under the given circumstances can be used.

According to variant d. of the process according to the invention a compound of the general formula (VII) is halogenated and the halomethyl derivative thus-obtained is, after or without isolation, cyclized. The leaving group represented by Z in the general formula (VII) is a usual protecting group of the amino group, e.g. an acyl group, preferably a lower alkanoyl group (e.g. acetyl or propionyl). The halogenation can be carried out in a known way (Belgian patent No. 697,976 and British patent No. 1,303,372) with the aid of an elementary halogen (e.g. chlorine or bromine) or N-halogen-succinimides (e.g. N-chloro- or N-bromo-succinimide). The halomethyl derivative thus-obtained can be cyclizated on the analogy of the compounds of the general formula (VI).

According to variant e. of the process according to the invention a compound of the general formula (VIII) is oxidized. The oxidization is carried out by methods known per se, e.g. with peracids (such as peracetic, perbenzoic, m-chloroperbenzoic acid, etc.). The reaction temperature can be varied between about 10° C. and 80° C. The compounds of the general formula (I) with basic character can be converted into their biologically acceptable acid addition salts formed with organic or mineral acids. Salt formation can be performed by reacting the base of the general formula (I) with an approximately equimolar amount of the corresponding acid in a suitable solvent.

The starting substances of the general formula (II) are known compounds (British patent No. 1,303,372). The starting substances of the general formulae (III) and (V) are similarly known [Ber. 84, 4771 (1951); Zs. Obscs. Him. 25, 16 (1955); Zabiczky, Jacob: The Chemistry of Amides Ch 10, 515 (Interscience Publ. 1970)]. The starting substances of the general formula (IV) are new and can be prepared on tha analogy of the process described in British patent No. 1,303,372. The starting substances of the general formulae (VI) and (VII) are also new and can be prepared by the process described in Belgian Pat. Nos. 697,976;721,728 and 721,724. The starting substances of the general formula (VIII) are new or can be prepared on the analogy of the known compounds.

The new compounds of the general formula (I) and their biologically acceptable acid addition salts can be used in animal husbandry due to their weight-gain increasing and antibacterial effects.

The new compounds of the invention can be used either locally or in a systemic manner for the prophylaxis or treatment of various bacterial infections. These compounds are active against a wide range of gram-positive or gram-negative bacteria, e.g. against the following microorganisms: Enterobacteriacese, such as Escherichia, e.g. E. coli, Pseudomonadacese, such as Pseudomonas aeruginosa, Micrococcacese, such as Staphylococcus aureus.

The minimum inhibiting concentration of the compounds of the general formula (I) against the strains listed above is between 0.5 $\gamma$/ml and 128 $\gamma$/ml.

The weight-gain increasing effect of the new compounds of the general formula (I) is shown in the following test. Pigs are used as test animals. For each test groups of 6 animals are used and each experiment with six pigs is repeated three times. The pigs of the test group are fed with a fodder comprising 50 mg/kg of the test compound of the general formula (I). The animals in each test group are fed with the same fodder and under identical conditions except the art and amount of the test compound incorporated into the fodder. The animals of the control group receive the same fodder but without test compound of the general formula (I). The results obtained are summarized in Table I.

TABLE I

| Test compound (Example No.) | Average daily weight-gain, related to the controls | Weight of fodder producing 1 kg of weight-gain, related to the controls |
| --- | --- | --- |
| 1 | 124.3 | 81.9 |
| 6 | 125.2 | 88.6 |

It appears from the above data that the weight-gain of the animals fed with a fodder containing the compounds of the invention is significantly higher than that of the pigs of the control group. At the same time the same weight-gain can be achieved with a considerably smaller amount of fodder when a compound of the general formula (I) is incorporated into the animal feed. This is a proof of an improved fodder utilization.

An important advantage of the compounds of the invention resides in the fact that they are evacuated from the animal organism within a considerably shorter time than the known quinoxaline-1,4-dioxide derivatives, i.e. their retention time is considerably shorter. This is a significant advantage from the aspects of animal husbandry.

The toxicity of the compounds of the general formula (I) against domestic animals is so low that they practically can be regarded as atoxic.

According to a further feature of the invention there are provided compositions for use in animal husbandry comprising as active ingredient an effective amount of a compound of the general formula (I), wherein R is as defined above, or a biologically acceptable acid addition salt of a compound of the general formula (I) with basic character in admixture with suitable inert solid or liquid carriers or diluents.

These compositions can be presented in forms generally used in veterinary practice, such as tablets, coated tablets, boluses, etc. These compositions may contain the usual inert carriers, diluents and additives and can be prepared by methods well known in the pharmaceutical industry.

The compositions of the present invention may be particularly fodder additives, fodder concentrates and fodders comprising as active ingredient in an effective amount a compound of the general formula (I), wherein R is as defined above, or a biologically acceptable acid addition salt of a compound of the general formula (I) with basic character in admixture with suitable edible solid or liquid carriers or diluents and additives.

According to a further feature of the invention there is provided a process for the preparation of fodder additives, fodder concentrates and fodders, which comprises admixing a compound of the general formula (I), wherein R is as defined above, or a biologically acceptable acid addition salt of a compound of the general formula (I) with basic character with a suitable edible solid or liquid carrier or diluent and additive generally used in the production of fodder additives and fodders.

As carrier or diluent any substance of vegetable or animal origin applicable in the feeding of animals or serving as fodder can be used. For this purpose e.g. wheat, rice, maize, soybean, alfalfa, barley, oats, rye can be used in appropriate forms (grits, groats, meal, bran, etc.), furthermore fish meal, meat meal, bone meal or mixtures thereof can be applied as well. One way advantageously use a fibre-free green plant fodder concentrate with high protein content (e.g. VEPEX$^R$).

As additives e.g. silicic acid, wetting agents, antioxidants, starch, dicalcium phosphate, calcium carbonate, sorbic acid, etc. can be used. As wetting agent e.g. nontoxic oils, preferably soybean oil, maize oil or mineral oil can be applied. Various alkylene glycols can also be used as wetting agent. The starch used may be wheat, maize or potato starch.

The fodder additives and concentrates may contain usual vitamins (e.g. vitamin A, $B_1$, $B_2$, $B_3$, $B_6$, $B_{12}$, E, K) and trace elements (e.g. Mn, Fe, Zn, Cu, I), too.

The active ingredient content of the compositions may vary within wide ranges. The fodder additives and concentrates may contain about 5–80% by weight, preferably about 10–50% by weight of the active ingredient of the general formula (I). The active ingredient content of the animal fodders ready for use may be about 1–400 ppm, preferably about 10–100 ppm.

The fodder additives and concentrates are diluted with suitable fodder components or are incorporated into suitable animal feeds to provide animal feeds ready for use.

The fodders according to the present invention can be used for the increase of weight gain and improvement of feed utilization of various domestic animals, such as pigs, lambs, cattle and poultry, particularly pigs.

Further details of the present invention are to be found in the following Examples without limiting the scope of the invention to the Examples.

EXAMPLE 1

Preparation of 2-methoxycarbonyl-1,2,3,4-tetrahydro-1-oxo-1H-pyridazino[4,5-b]quinoxaline-5,10 dioxide a. 32.7 g (0.1 mole) of 3-bromomethyl-quinoxaline-2-ethyl-carboxylate-1,4-dioxide and 9 g (0.1 mole) of methyl carbazate are reacted in 200 ml of methanol in the presence of 10.1 g (0.1 mole) of triethylamine at room temperature. When the exoterm reaction has completed the separated crystals are filtered off. 14.5 g of the desired compound are obtained.
Yield: 50%
M.p.: 254°–256° C.

b. One proceeds as described in variant a. with the difference that 3-bromomethyl-quinoxaline-(p-toluenesulfonyl)-carboxylate is used as starting substance.
Yield: 73%
M.p.: 253°–254° C.

EXAMPLE 2

Preparation of 2-[3′,4′,5′-trimethoxybenzoyl]-1,2,3,4-tetrahydro-1-oxo-1H-pyridazino[4,5-b]quinoxaline-5,10-dioxide A mixture of 16.4 g (0.05 moles) of 3-bromomethyl-quinoxaline-2-ethyl-carboxylate-1,4-dioxide, 11.3 g (0.05 moles) of 3,4,5-trimethoxybenzoic hydrazide, 6.05 g (0.05 moles) of N,N-dimethyl-aniline and 150 ml of isopropanol are stirred at room temperature. The separated product is filtered off. 16 g of the desired compound are obtained.
Yield: 75%
M.p.: 200°–201° C.

EXAMPLE 3

Preparation of 2-cyclopropanecarbonyl-1,2,3,4-tetrahydro-1-oxo-1H-pyridazino[4,5-b]quinoxaline-5,10-dioxide A mixture of 14.1 g (0.05 moles) of 3-chloromethyl-quinoxaline-2-ethyl-carboxylate-1,4-dioxide, 5 g (0.05 moles) of cyclopropanecarboxylic hydrazide, 5.06 g (0.05 moles) of triethylamine and 80 ml of n-butanol is reacted at 60° C. for 3 hours. 10.5 g (70%) of the desired compound are obtained.
M.p.: 239°–240° C.

EXAMPLE 4

Preparation of 2-benzoyl-1,2,3,4-tetrahydro-1-oxo-1H-pyridazino[4,5-b]quinoxaline-5,10-dioxide a. A mixture of 16.4 g (0.05 moles) of 3-bromomethyl-quinoxaline-2-ethyl-carboxylate-1,4-dioxide, 6.8 g (0.05 moles) of benzoic hydrazide, 5.06 g (0.05 moles) of triethylamine and 150 ml of acetonitrile is reacted at room temperature. When the exothermic reaction is completed the separated crystals are filtered off. 11 g of the desired compound are obtained.
Yield: 65.4 g
M.p.: 236°–237° C.

b. 19.1 g (0.05 moles) of 3-benzoyl-hydrazino-methyl-quinoxaline-2-ethyl-carboxylate-1,4-dioxide are boiled in benzene in the presence of sodium methylate for 12 hours. The separated product is filtered off. 12.5 g of the desired product are obtained.
Yield: 73.8%
M.p.: 236°–237° C.

EXAMPLE 5

Preparation of 2-phenoxyacetyl-1,2,3,4-tetrahydro-1-oxo-1H-pyridazino[4,5-b]quinoxaline-5,10-dioxide a. One proceeds as described in Example 4a, with the difference that phenylacetic hydrazide is used instead of benzoic hydrazide. The desired product is obtained with a yield of 65%.
M.p.: 230°–231° C.

b. A mixture of 19.2 g (0.1 mole) of 1,2,3,4-tetrahydro-1-oxo-1H-pyridazino[4,5-b]quinoxaline-5,10-dioxide, 15.4 g (0.1 mole) of phenylacetic chloride, 10.12 g (0.1 mole) of triethylamine and 70 ml of benzene is boiled, then the separated compound is filtered off.
Yield: 65%
M.p.: 231°–232° C.

EXAMPLE 6

Preparation of 2-isonicotinoyl-1,2,3,4-tetrahydro-1-oxo-1H-pyridazino[4,5-b]quinoxaline-5,10-dioxide One proceeds as described in Example 2, with the difference that isonicotinic hydrazide is used as starting substance instead of 3,4,5-trimethoxybenzoic hydrazide. The compound is obtained with a yield of 60%.
M.p.: 237°–238° C.

EXAMPPLE 7

A premix for supplementing pig fodder is prepared with the following composition:

| Components | Amounts |
| --- | --- |
| Vitamin A | 3,000,000 IU |
| Vitamin $D_3$ | 600,000 IU |
| Vitamin E | 4,000 IU |
| Vitamin $K_3$ | 400 mg |
| Vitamin $B_1$ | 600 mg |
| Vitamin $B_2$ | 800 mg |
| Vitamin $B_3$ | 2,000 mg |
| Vitamin $B_6$ | 800 mg |
| Vitamin $B_{12}$ | 10 mg |
| Niacine | 4,000 mg |
| Choline chloride | 60,000 mg |
| Active agent according to Example 1 | 10,000 mg |
| Butylhydroxytoluene (antioxidant) | 30,000 mg |
| Flavouring substances | 8,000 mg |
| Sodium saccharate | 30.000 mg |
| Trace elements: | |
| Mn | 8,000 mg |
| Fe | 30,000 mg |
| Zn | 20,000 mg |
| Cu | 6,000 mg |
| I | 100 mg |
| Twice-ground bran ad | 1,000 g |

This premix of vitamins and trace elements is admixed with the basal fodder in a concentration of 0.5 kg per 100 kg.

EXAMPLE 8

A premix for supplementing piglet fodder is prepared with the following composition:

| Components | Amounts |
|---|---|
| Vitamin A | 1,200,000 IU |
| Vitamine $D_3$ | 300,000 IU |
| Vitamin E | 2,000 IU |
| Vitamine $B_2$ | 600 mg |
| Vitamin $B_3$ | 2,000 mg |
| Vitamine $B_{12}$ | 5 mg |
| Niacine | 3,000 mg |
| Choline chloride | 40,000 mg |
| Active agent according to Example 1 | 10,000 mg |
| Butylhydroxytoluene (antioxidant) | 30,000 mg |
| Trace elements: | |
| Mn | 6,000 mg |
| Fe | 10,000 mg |
| Zn | 15,000 mg |
| Cu | 30,000 mg |
| I | 100 mg |
| Twice-ground bran ad | 1,000 g |

This premix of vitamins and trace elements is admixed with the basal fodder in a concentration of 0.5 kg per 100 kg.

EXAMPLE 9

0.5 kg of a premix as described in Example 7 are admixed with 100.0 kg of a basal fodder with the following composition:

| Components | Amounts, kg |
|---|---|
| Maize | 37.6 |
| Barley | 25.4 |
| Wheat | 6.0 |
| Oats | 5.0 |
| Soybean | 13.0 |
| Fish meal | 6.0 |
| Bran | 2.4 |
| Fat powder | 1.5 |
| Premix of minerals[x] | 1.0 |
| Lime (fodder quality) | 1.0 |
| Sodium chloride | 0.5 |
| Biolisine | 0.1 |
| Premix according to Example 7 | 0.5 |
| Total weight: | 100.0 kg |

The active agent content of the resulting pig fodder is 50 ppm.
[x]The composition of the premix of minerals is as follows:

| Components | Amounts, % |
|---|---|
| Dicalcium phosphate | 55.0 |
| Monocalcium phosphate | 40.0 |
| Calcium carbonate | 5.0 |

EXAMPLE 10

0.5 kg of a premix as described in Example 8 are admixed with 100.0 kg of a basal fodder with the following composition:

| Components | Amounts, kg |
|---|---|
| Maize | 25.0 |
| Wheat | 34.0 |
| Extracted soybean | 18.0 |
| Milk powder | 9.9 |
| Fish meal | 4.0 |
| Yeast (fodder quality) | 2.0 |
| Fat powder | 3.4 |

-continued

| Components | Amounts, kg |
|---|---|
| Premix of minerals according to Example 9 | 1.8 |
| Lime (fodder quality) | 1.0 |
| Sodium chloride (fodder quality) | 0.4 |
| Premix according to Example 25 | 0.5 |
| Total weight: | 100.0 kg |

The active agent content of the resulting piglet fodder is 50 ppm.

EXAMPLE 11

400 kg of a pre-ground soybean meal are filled into a mixer, 3.1 kg of soybean oil are added under stirring, and the mixture is stirred until the solids get coated with oil. Thereafter 9.1 kg of an active agent according to Example 6 are added and the mixture is stirred until a homogeneous blend is obtained. Finally 9.0 kg of soybean oil are added, and the mixture is homogenized again.

EXAMPLE 12

0.5 kg of an active agent according to Example 6 are added to 40 kg of corn meal under stirring, and simultaneously 3.0 kg of propylene glycol are sprayed into the mixture. Thereafter 1.4 kg of dicalcium phosphate are added and the mixture is homogenized.

EXAMPLE 13

10 kg of alfalfa meal and 15 kg of VEPEX[R] are stirred for 20 minutes, thereafter 1 kg of maize oil is started to spray into the mixture with an even speed so that spraying is continued during the introduction of the following additional components: 2.5 kg of an active agent according to Example 1, 10 kg of maize starch, 2.5 kg of the above active agent, 0.3 kg of silicon dioxide, 0.6 kg of ascorbic acid, 9 kg of maize starch and 2.5 kg of the above active agent. Thereafter the mixture is stirred for additional 5 minutes.

EXAMPLE 14

One proceeds as described in Example 11 with the difference that buthylene glycol is applied as wetting agent instead of soybean oil.

EXAMPLE 15 a. 3.5 kg of potato starch are admixed with 2.9 kg of an active agent according to Example 2. 0.05 kg of mineral oil are sprayed into the mixture, thereafter 0.2 kg of sorbic acid, 0.4 kg of silicon dioxide and 0.1 kg of calcium propionate are added, and the mixture is stirred for additional 2 minutes.

b. 4.2 kg of fish meal are admixed with 22 kg of rye bran, 0.6 kg of mineral oil are sprayed into the mixture, thereafter 4 kg of a mixture prepared according to point a., 10 kg of maize meal, 4 kg of a mixture prepared according to point a. and 9 kg of maize meal are introduced under stirring. Finally 0.6 kg of mineral oil are spayed into the mixture.

EXAMPLE 16

100 kg of wheat bran, 10 kg of an active agent according to Example 5, 2.5 kg of calcium carbonate, 0.15 kg of α-tocopherol and 0.4 kg of calcium propionate are homogenized with 4 kg of propylene glycol.

EXAMPLE 17

10 kg of soybean meal and 0.6 kg of an active agent according to Example 3 are homogenized with 2.5 kg of butylene glycol.

EXAMPLE 18

50 kg of soybean meal, 6 kg of an active agent according to Example 1, 0.5 kg of silicon dioxide and 0.2 kg of calcium propionate are homogenized with 1.6 kg of soybean oil.

What we claimed is:

1. Pyridazino[4,5-b]quinoxaline-5,10-dioxide derivatives of the formula I

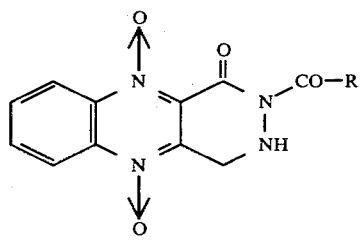

wherein
R represents a $C_{1-20}$ alkyl, a $C_{1-6}$ alkoxy group, a $C_{6-10}$ aryl group optionally mono or disubstituted by $C_{1-6}$ alkoxy, $C_{1-6}$ alkyl, nitro, amino, hydroxy or halogen, a phenyl-$C_{1-3}$ alkyl/, a $C_{3-7}$ cycloalkyl or a 5 or 6 membered heterocyclic group containing one or two nitrogen and/or oxygen and/or sulfur atoms and selected from the group consisting of 2-, 3- or 4-pyridyl, pyrazinyl, pyridazinyl, furyl, thienyl, thiazolyl and imidazolyl groups, and biologically acceptable acid addition salts of the compouns of the formula I.

2. Methoxycarbonyl-1,2,3,4-tetrahydro-1-oxo-1H-pyridazino[4,5-b]quinoxaline-5,10-dioxide.

3. Isonicotinoyl-1,2,3,4-tetrahydro-1-oxo-1H-pyridazino[4,5-b]quinoxaline-5,10-dioxide.

4. Compositions for use in animal husbandry as a fodder additive and/or as an anti-bacterial agent comprising as active ingredient an effective amount of a compound of the formula I, wherein R has the same meanings as defined in claim 1, or a biologically acceptable acid addition salt thereof in admixture with suitable inert solid or liquid carriers or diluents.

5. Fodder additives, fodder concentrates and fodders having antimicrobial and/or weight-gain increasing effects comprising a nutrient and as active ingredient an effective amount of a compound of the formula I, wherein R is as defined in claim 1, or a biologically acceptable acid addition salt thereof in admixture with suitable inert solid or liquid carriers or diluents.

6. A process for increasing the weight-gain and the fodder-utilization of animals, consisting of feeding the said animals with a fodder as claimed in claim 5.

* * * * *

UNITED STATES PATENT AND TRADEMARK OFFICE
CERTIFICATE OF CORRECTION

PATENT NO. : 4,404,204

DATED : September 13, 1983

INVENTOR(S) : Pal BENKO; Daniel BOZSING; Janos GUNDEL and Karoly MAGYAR

It is certified that error appears in the above-identified patent and that said Letters Patent is hereby corrected as shown below:

On the title page, correct line [73] to read as follows:

Assignee: --Egyt Gyogyszervegyeszeti Gyar, Hungary--.

Signed and Sealed this

Fifteenth Day of November 1983

[SEAL]

Attest:

GERALD J. MOSSINGHOFF

Attesting Officer     Commissioner of Patents and Trademarks